(12) United States Patent
De Winne et al.

(10) Patent No.: US 8,217,206 B2
(45) Date of Patent: Jul. 10, 2012

(54) PROCESS FOR THE SELECTIVE OXIDATION OF METHANE

(75) Inventors: Hendrik De Winne, Deurne (BE); Pierre Jacobs, Gooik (BE); Bert Sels, Balen (BE); Walter Vermeiren, Houthalen (BE)

(73) Assignee: Total Petrochemicals Research Feluy, Seneffe (Feluy) (BE)

( * ) Notice: Subject to any disclaimer, the term of this patent is extended or adjusted under 35 U.S.C. 154(b) by 0 days.

(21) Appl. No.: 12/669,566

(22) PCT Filed: Jul. 4, 2008

(86) PCT No.: PCT/EP2008/058690
§ 371 (c)(1),
(2), (4) Date: Jul. 7, 2010

(87) PCT Pub. No.: WO2009/010407
PCT Pub. Date: Jan. 22, 2009

(65) Prior Publication Data
US 2010/0280289 A1    Nov. 4, 2010

(30) Foreign Application Priority Data
Jul. 19, 2007  (EP) .................... 07112759

(51) Int. Cl.
*C07C 27/10* (2006.01)
*C07C 29/48* (2006.01)
*B01J 19/00* (2006.01)
*B01J 8/00* (2006.01)

(52) U.S. Cl. .................... 568/910; 568/910.5; 422/241; 422/651; 422/654

(58) Field of Classification Search .................. 568/910, 568/910.5; 422/241, 651, 654
See application file for complete search history.

(56) References Cited

U.S. PATENT DOCUMENTS

| 4,618,732 | A | * | 10/1986 | Gesser et al. | ............... 568/910.5 |
| 4,973,777 | A | | 11/1990 | Alagy et al. | |
| 4,982,023 | A | * | 1/1991 | Han et al. | ................... 568/910.5 |
| 5,220,080 | A | | 6/1993 | Lyons et al. | |
| 2008/0299017 | A1 | | 12/2008 | Sattler et al. | |

FOREIGN PATENT DOCUMENTS

| GB | 1274653 A | 5/1972 |
| WO | 2007025766 A | 3/2007 |

* cited by examiner

*Primary Examiner* — Sikarl Witherspoon

(57) ABSTRACT

The present invention is a process for converting methane to methanol, comprising:
feeding methane and gaseous air or oxygen or gaseous air enriched with oxygen to a reactor under an elevated pressure;
said reactor having an internal surface, made of silica or coated with silica, surrounding a zone in which said gases react; and
reacting said gases in said reaction zone at an elevated temperature at conditions effective to produce methanol and for valuable oxygenates.
Advantageously the internal surface is made of quartz or coated with quartz
Advantageously the internal surface, made of silica (advantageously quartz) or coated with silica (advantageously quartz), is treated with HF before the conversion of methane to methanol.
Advantageously the reaction is carried out in the absence in said reaction zone of any added material which measurably affects the rate of the reaction or the yield of the product.
Advantageously the reactor is operated under a pressure from 1 to 7.5 MPa.
Advantageously the reactor is operated at a temperature from 300° C. to 600° C.
Advantageously the reactor is operated at a residence time from 0.1 to 100 s.
Advantageously the reactor is operated at a methane to oxygen molar ratio from 1 to 50.
The present invention also relates to a reactor having an internal surface made of silica (advantageously quartz) or coated with silica (advantageously quartz).

19 Claims, 14 Drawing Sheets

▲ section 1
△ section 2
× section 3
○ section 4
■ section 5
○ no quartz packing

● empty HSQ + HF tube
◇ filled with untreated VWF quartz granules
◆ filled with HF treated VWF quartz granules ● 0.5 MPa
▲ 0.8 MPa
■ 1.2 MPa ◆ CO
▲ CO₂
× C₂H₆+C₂H₄
■ HCHO
● CH₃OH (CH₄/O₂ = 9, T$_{max}$= 480)

PROCESS FOR THE SELECTIVE OXIDATION OF METHANE

BACKGROUND OF THE INVENTION

Despite its natural abundance, only a small part of the extracted natural gas is used for chemical production. Since most natural gas sources are situated in remote areas or offshore places far from consumption, the lack of infrastructure is the greatest barrier to increase natural gas usage worldwide. The natural gas that is associated with crude oil, is now re-injected to enhance the crude oil extraction or is flared. Although natural gas distribution occurs through pipelines, this still requires the exploration areas to be easy reachable and the pipelines to be installed on easy accessible grounds. This natural gas is stored at 8-30 MPa. Another transportation option consists in liquefaction of natural gas (LNG) under low temperatures (−160° C.) which requires equipped tankerships. Gas transportation from remote areas is associated with high costs. Because of the high investment and transport costs, there is a large interest in the conversion of natural gas into more interesting products such as liquid oxygenates or higher hydrocarbons. The process of the present invention relates to a process for selective oxidation of methane, advantageously to obtain methanol and or valuable oxygenates.

BACKGROUND OF THE INVENTION

U.S. Pat. No. 4,618,732 provides a process for the direct conversion of natural gas to methanol. This is achieved by reacting natural gas with oxygen or air in the absence of a catalyst in an inert reactor at an elevated temperature and pressure. To obtain a high yield of methanol, the reactant gases, i.e. natural gas and oxygen or air, are first intimately mixed. In another aspect, said prior art provides apparatus for carrying out a method of converting natural gas to methanol. The apparatus comprises an inert reactor and means for intimately mixing the oxygen or air and natural gas prior to their introduction into the reactor. Means are also provided to ensure that the gases reach at suitable elevated temperature and pressure in the reactor. By the term "inert reactor" is meant a reactor that has internal surfaces made of, or coated with, a material which has no substantial adverse effect upon the methanol yields or selectivity. Preferably, the reactor is made of stainless steel lined with glass or polytetrafluoroethylene. The pressures employed in the reactor are generally in the range of 10 to 100 atmospheres, more preferably 10 to 60 atmospheres, and even more preferably 10 to 50 atmospheres. The temperature employed in the reactor is generally in the range of 300° C. to 500° C., more preferably 350° C. to 450° C. The contact time of the gases depends to some extent on the temperature, pressure and relative oxygen concentration, but the normal contact time is within the range of 2 to 1000 seconds, preferably 5 to 15 seconds, and more preferably about 10 seconds. According to FIG. 5 at 350° C. the yield of CO and $CO_2$ are similar. According to FIG. 6 at 65 atmospheres and 410-430° C. the ratio of CO to $CO_2$ is about 2.

U.S. Pat. No. 4,982,023 describes the synthesis of methanol by the homogeneous direct partial oxidation of natural gas or other source of methane when the reactor space is filled with inert, refractory inorganic particles. The reactor is a 16.5 mm i.d. Pyrex-lined tube. Both the yield and the selectivity in the direct homogeneous partial oxidation of a gaseous feed comprising methane and gaseous oxygen are improved when the empty reactor is packed with a low surface area solid such as sand. The runs were performed using natural gas feed comprising 95.66 w % methane.

Example 1 is made with an empty tube at 68 bars, 360° C., 6.4% $O_2$ in the feed and 4 minutes residence time. Conversion is 5.5%, CO selectivity 49.4%, $CO_2$ selectivity 21.8%, methanol selectivity 25.8% and other oxygenates 3%.

Example 2 is made with a tube filled with sand, at 68 bars, 400° C., 7% $O_2$ in the feed and 4 minutes residence time. Conversion is 5.9%, CO selectivity 40%, $CO_2$ selectivity 21.7%, methanol selectivity 27.2% and other oxygenates 11.1%.

WO 00-007718 describes a catalytic composition, optionally supported on an inert material, characterized in that it comprises (i) oxides and/or hydroxides of a first metal (M1) and (ii) halides of a second metal (M2), wherein M1 and M2, the same or different, are selected from metals belonging to groups IIa, IIb, IVb, VIII, Ib, Va, Lanthanides, and relative mixtures. It also relates to the selective transformation of methane on said catalytic composition, in example 7 the reactor is made of quartz.

U.S. Pat. No. 4,918,249, GB 1244001, U.S. Pat. No. 5,414,157 and GB 1398385 also relate to the oxidation of methane on catalysts.

It has now been discovered that the methane oxidation to methanol could be made in a silica tube, advantageously a quartz tube, advantageously empty. Advantageously the quartz tube is HF treated.

- a quartz-tube that is treated with HF aqueous solution is more active and selective in the selective methane oxidation into mainly methanol and carbon monoxide. Only small amounts of formaldehyde and carbon dioxide are produced.
- it is preferable that the quartz reactor tube is empty. When filled with quartz particles, the methane conversion is significantly reduced.
- when smaller diameter quartz tubes are used the conversion and selectivity increases, so the surface-to-volume ratio appears to be important.

SUMMARY OF THE INVENTION

The present invention is a process for converting methane to methanol, comprising:

feeding methane and gaseous air or oxygen or gaseous air enriched with oxygen to a reactor under an elevated pressure; said reactor having an internal surface, made of silica or coated with silica, surrounding a zone in which said gases react; and reacting said gases in said reaction zone at an elevated temperature at conditions effective to produce methanol and/or valuable oxygenates.

Silica means a composition consisting essentially of silica and comprising no component having an adverse effect to the conversion of methane to methanol. Advantageously this is pure silica under the usual meaning of the man skilled in the art.

Silica can be amorphous, crystalline or of any structure or can be quartz. The internal surface can be made partly with a type of silica and partly with another type of silica. The internal surface can be coated partly with a type of silica and partly with another type of silica. The internal surface can be a combination of a part made with a type of silica and a part coated with another or same type of silica.

Advantageously the internal surface is made of quartz or coated with quartz

Advantageously the internal surface, made of silica (advantageously quartz) or coated with silica (advantageously quartz), is treated with HF before the conversion of methane to methanol.

Advantageously the reaction is carried out in the absence in said reaction zone of any added material which measurably affects the rate of the reaction or the yield of the product.

Advantageously the reactor is operated under a pressure from 0.1 to 7.5 MPa. Advantageously the reactor is operated at a temperature from 300° C. to 600° C. Advantageously the reactor is operated at a residence time from 0.1 to 100 s. Advantageously the reactor is operated at a methane to oxygen molar ratio from 1 to 50.

Advantageously the reactor is operated under a pressure from 0.1 to 7.5 MPa, a temperature from 300° C. to 600° C., a residence time from 0.1 to 100 s and a methane to oxygen molar ratio from 1 to 50.

The present invention also relates to a reactor having an internal surface made of silica (advantageously quartz) or coated with silica (advantageously quartz). The internal surface of the reactor can be made partly with a type of silica and partly with another type of silica. The internal surface of the reactor can be coated partly with a type of silica and partly with another type of silica. The internal surface of the reactor can be a combination of a part made with a type of silica and a part coated with another or same type of silica.

DETAILED DESCRIPTION OF THE INVENTION

Although the reactor can be made of any type of silica or coated with silica, the following description of the reactor is focused on quartz as an example. This is only to illustrate the present invention without limiting the scope thereof.

The reactor may consist of a tubular quartz reactor that is straight in nature. The tube can consist of plain quartz or any other suitable material that is coated with quartz and has been optionally treated with an acidic HF solution. The industrial reactor can consist of many tubes of a given diameter placed in parallel in a big reactor vessel as to obtain a multi-tubular reactor with specific surface-to-volume ratio. The inner diameter of the individual quartz tubes can be from 0.1 to 1000 mm, preferentially from 1 to 100 mm and most preferentially from 2 to 10 mm. The length of the reactor tubes is such that the desired diameter and desired residence time can be applied. The diameter is the most important operation parameter and hence the residence time can be controlled by adjusting the tube length. The wall thickness is such that the mechanical strength of the tube is sufficient to be handled and placed in a commercial reactor vessel.

Figure 1:
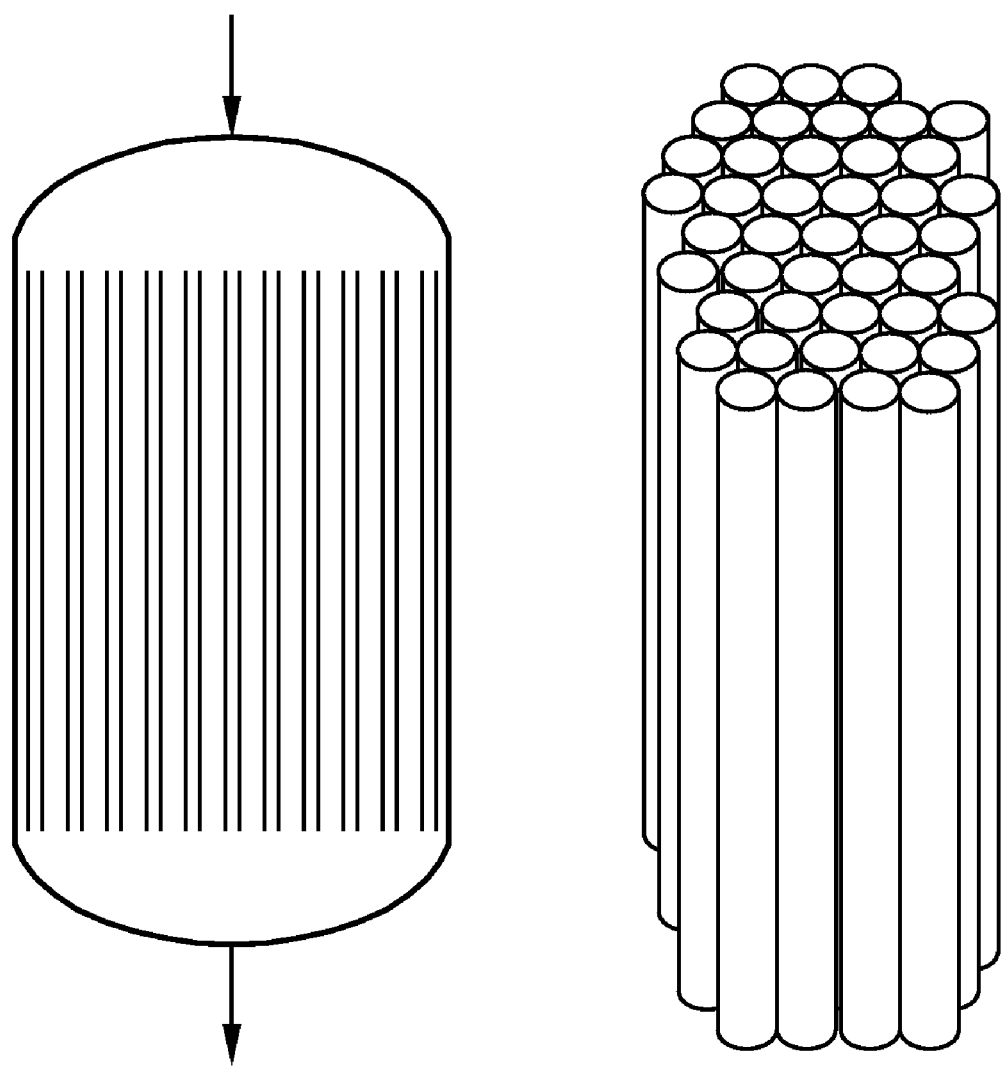
FIG. 1 is a drawing of a reactor configuration consisting of many quartz tubes placed in a larger reactor vessel.
Figure 2:
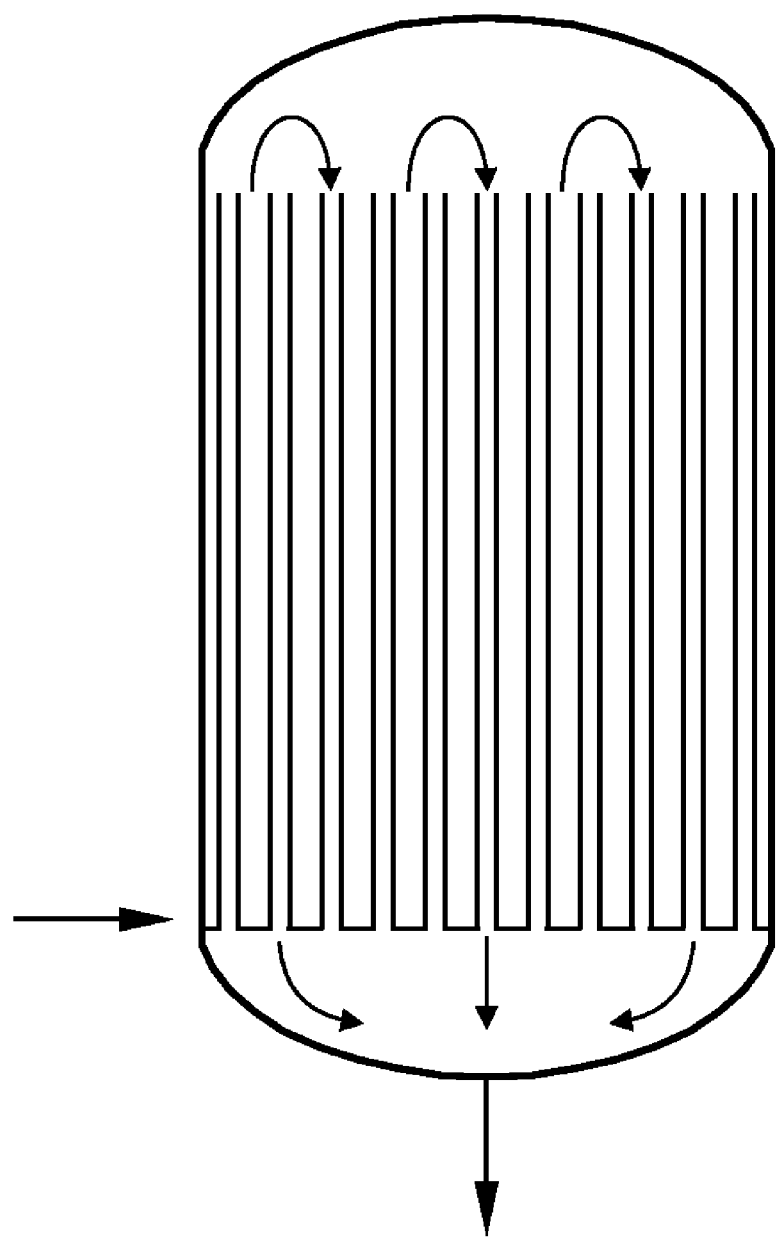
FIG. 2 is a drawing of a reactor configuration consisting of many quartz tubes placed in a larger reactor vessel with counter current flow directions.
Figure 3:
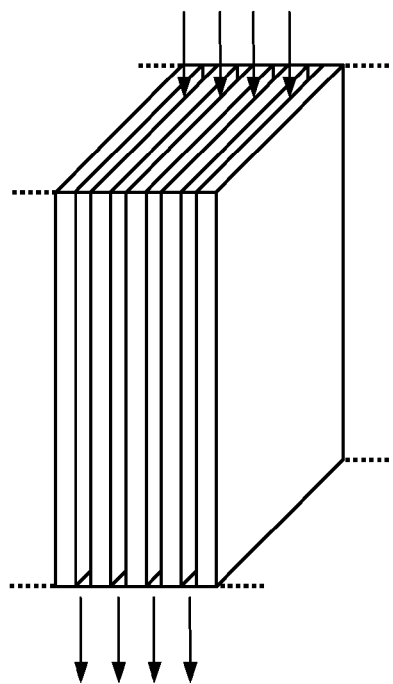
FIG. 3 is a drawing of a reactor configuration consisting of many plates made of quartz or any other suitable material coated with quartz placed in a larger reactor vessel.
Figure 4:
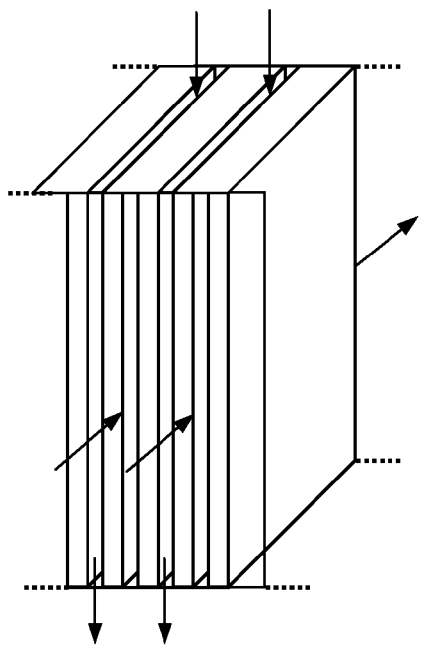
FIG. 4 is a drawing of a reactor configuration consisting of many plates made of quartz or any other suitable material coated with quartz placed in a larger reactor vessel. The plates are placed in such a manner that heat exchange can be applied between a cold entering gas and a hot leaving gas.

The reactants enter on one side of the reactor tubes and the reaction products leave at the opposite side. The flow direction can be in any way, top-down, down-top or even horizontally (see FIG. 1). The reactor tubes can also be placed parallel and linked at the bottom or top to a manifold device so that only reactants can flow in one direction inside the tube and in the other direction at the outside of the tube. The inlet of the reactants is hence laterally in the reactor vessel. This configuration allows to heat up the reactant mixture flowing at the outside of the tube by heat transfer through the tube wall with the hot reaction product flowing at the inside of the reactor tube. The reactant flow direction can also be the reverse: cold reactant flowing inside and hot reaction product outside of the tubes (see FIG. 2). In still another reactor configuration, the reactor consist of multiple plates, either made from quartz or from any other suitable material coated with a quartz layer and treated with HF acid solution. The distance between the plates is such that the optimum surface-to-volume ratio and residence time is obtained (see FIG. 3). Again the plates can be configured such that a heat exchange can be applied between a cold entering gas and a hot leaving gas (see FIG. 4).

In a specific embodiment said reactor is a micro-reactor as described in prior art but coated with silica, advantageously quartz.

As regards the quartz the man skilled in the art can easily select among the material available on the market by making routine experiments (see ex 1). Similar experiments can be made on quartz coated surfaces. Oxidation of methane is highly improved when the internal surface, made of quartz or coated with quartz, is treated by HF.

As regards the HF treatment it is made by an aqueous HF solution. Advantageously said aqueous HF solution contains from 0.1 to 25 wt % of HF, preferentially from 3 to 20% and most preferentially from 5 to 10%. The aqueous solution may also contain other acids, exhibiting complexing power that can remove metals from the surface. These are sulphuric acid, nitric acid and phosphorus acid or phosphonic acid. These can be present in concentrations of each 0.1 to 25 wt %, preferentially from 3 to 20%. Duration of treatment can be from 0.01 to 5 hours, most preferentially from 0.05 to 2 hours. The temperature of the treatment can be from 0 to 100° C., most preferentially from 10 to 50° C.

A typical treatment, taken into account the concentrations of the individual acids, is:

| Acids solution | amount | active acid concentration |
|---|---|---|
| HF @25% | 20% | 5% |
| H2PHO3 phosphonic acid @75% | 10% | 7.5% |
| H3PO4 phosphoric acid @60% | 10% | 6% |

This treatment is carried out in a polypropylene vessel during 10 minutes at room temperature.

The HF treatment improves the methane conversion and improves the selectivity for oxygenates. It also increases the methanol/formaldehyde ratio.

As regards the methane it could be natural gas or any gas containing a major proportion of methane. It would not depart from the scope of the invention if there are higher hydrocarbons in addition of the methane.

The methane to oxygen molar ratio is advantageously from 1 to 50, preferentially from 2 to 20 and most preferentially from 3 to 10. The reactor can be fed with gaseous air or oxygen or gaseous air enriched with oxygen.

Residence time in the reactor at the required reaction temperature and pressure is advantageously from 0.1 to 100 seconds, preferentially from 1 to 75 seconds and most preferentially from 2 to 20 seconds.

The reaction pressure is advantageously from 1 to 75 bars, preferentially from 2 to 50 bars and most preferentially from 4 to 25 bars.

The temperature is advantageously between 300° C. to 600° C. and preferably between 400 and 450° C.

Operating conditions can be any combination of the various ranges of the above parameters.

When the temperature increases the methane conversion increases but the selectivity in methanol decreases.

Advantageously the reaction is carried out in the absence in said reaction zone of any added material which measurably affects the rate of the reaction or the yield of the product. By way of example when the reaction is made in the inner part of a tube the tube is advantageously empty.

The process of the present invention make more CO than $CO_2$. CO has still a value and can be used for the production of hydrogen through the watergas shift reaction:

$$CO+H_2O \leftrightarrow CO_2+H_2$$

CO can also be added to a conventional methanol synthesis process. When steam methane reforming is applied, the synthesis gas has a SN=$(H_2-CO_2)/(CO+CO_2)$ ratio of close to 3 or a $H_2/CO$ ratio of 3 or higher. Methanol synthesis only requires a SN ratio of slightly higher than 2. By adding the CO, produced in the selective methane oxidation to methanol to the synthesis gas coming from a steam methane reforming, more methanol can be made. Moreover, a highly exothermic selective methane oxidation with oxygen can be integrated with the endothermic methane steam reforming.

EXAMPLES

The partial methane oxidation (PMO) reaction was carried out in a continuous flow reactor by sending a mixture of methane and oxygen through a tubular reactor. Conversions and selectivities are reported on carbon-basis.

Example 1

Comparison Between Commercially Available Quartz Tubes

Different types of quartz tubes with identical dimensions (internal diameter of 3 mm), obtained from different suppliers or with different quartz composition (Table 1), were tested for the homogeneous gas phase reaction.

TABLE 1

Impurities and hydroxyl concentrations (in ppm) in different types of quartz tubes as obtained from the manufacturer.

| Quartz Type | Manufacturer | W | Al | Ca | Fe | K | Li | Mg | Mn | Na | Ti | Zr | OH |
|---|---|---|---|---|---|---|---|---|---|---|---|---|---|
| $GE_1$ | General Electrics | yes | 15 | 0.5 | 0.3 | 1.5 | 1 | 0.2 | 0.1 | 1.3 | 0.9 | 1.5 | <5 |
| $GE_2$ | General Electrics | no | 15 | 0.5 | 0.3 | 1.5 | 1 | 0.2 | 0.1 | 1.3 | 0.9 | 1.5 | 15-45 |
| HSQ* | Heraeus | no | — | 0.2-1 | 0.1-0.3 | 0.1-0.5 | 0.5-1 | 0.1-0.2 | 0 | 0.1-0.2 | 0 | 0 | 30 |
| PH | Philips | yes | 16 | 0.8 | 0.8 | 0.9 | 0.7 | 0 | 0 | 0.9 | 1.5 | — | <5 |
| PN | Ilmenau | — | 15 | 0.8 | 0.3 | 0.9 | 0.7 | — | — | 0.9 | 1.4 | 0 | 15-45 |
| PS | Ilmenau | — | 8 | 0.2 | 0.4 | 0.3 | 0.4 | — | — | 5 | <0.2 | — | 5-15 |

Figure 5:
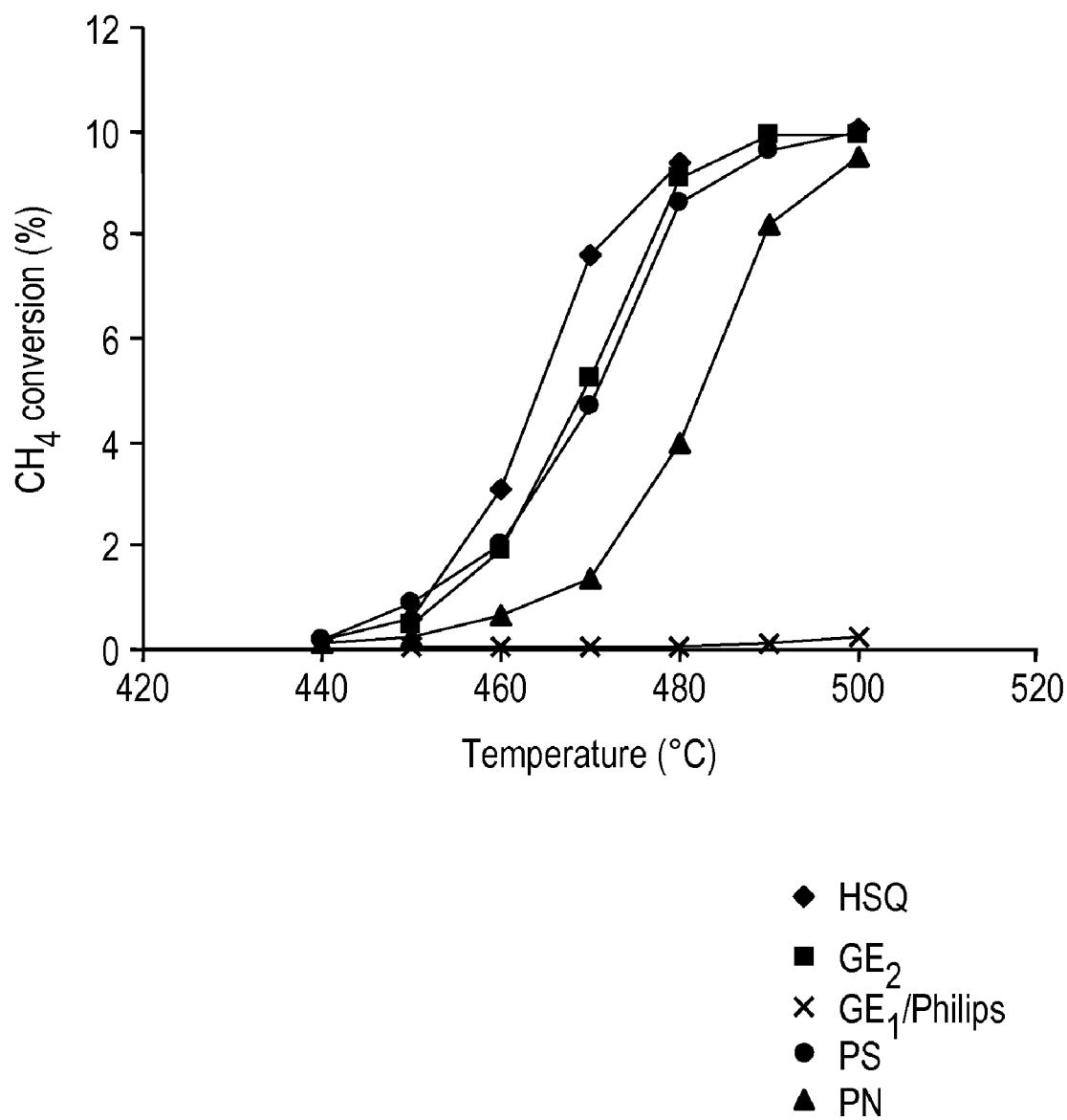
FIG. 5 is a graph of Temperature versus Methane conversion for different types of quartz tubes with identical dimension, as described in Example 1.

— not known
*Cr, Cu, As concentration are below 0.06, 0.02 and 0.002 ppm, respectively The results are shown in FIG. 5. The temperature, at which a certain methane conversion or 100% oxygen conversion is reached, depends clearly on the type of quartz tube used. No PMO (partial methane oxidation) reaction occurs in the General Electrics 1 ($GE_1$) and Philips (PH) quartz tubes at 0.5 MPa and temperatures below 500° C., while there is an obvious activity for the homogeneous gas reaction in other quartz tubes. There is already a methane conversion of 0.9% at 450° C. for the Heraeus 300 (HSQ) quartz. The order of activity inside the different reactor quartz tubes is as follows: HSQ>$GE_2$≈PS>PN>>PH≈$GE_1$.

Figure 6:
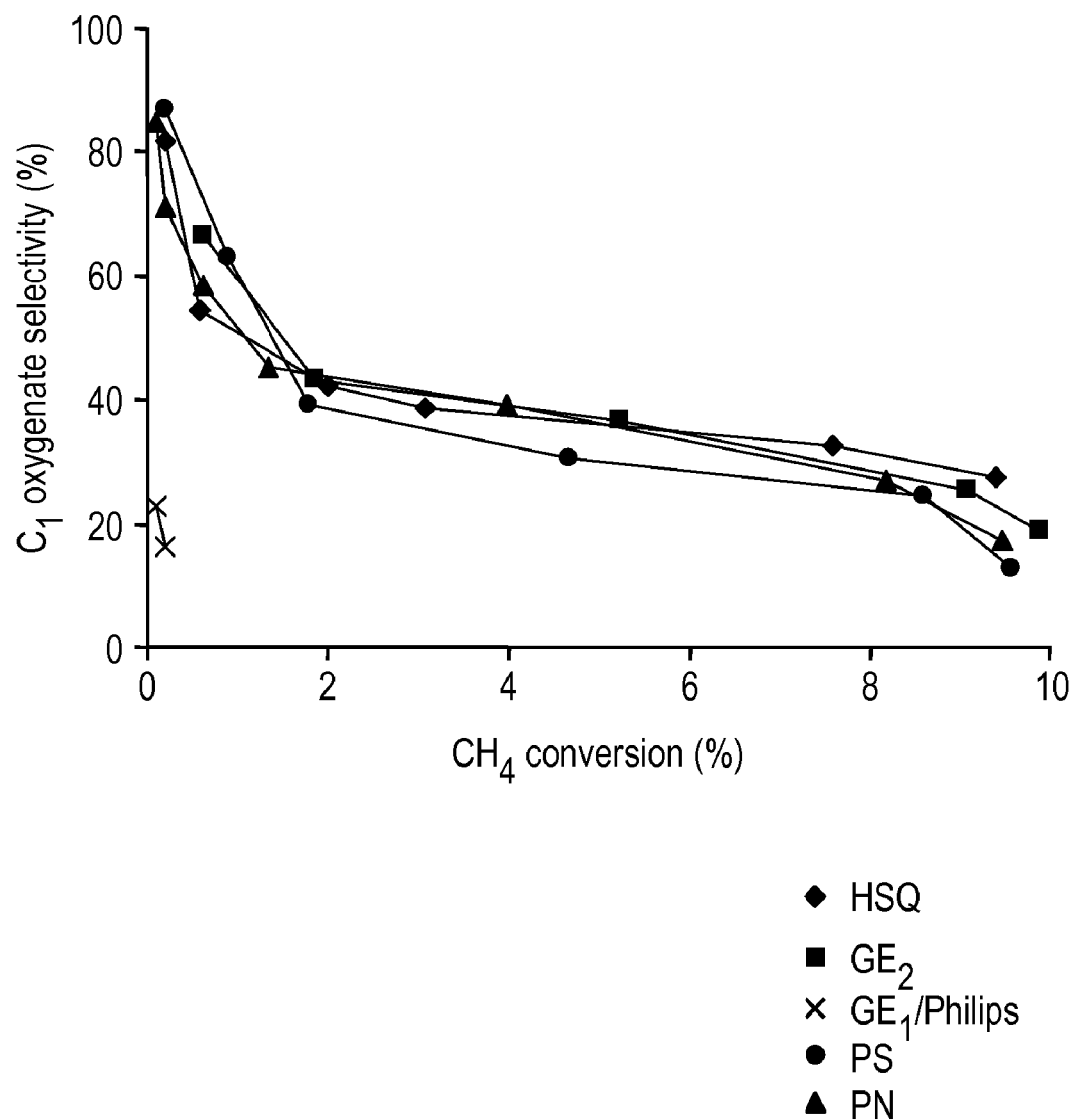
FIG. 6 is a graph of Methane conversion versus $C_1$ oxygenate selectivity for different types of quartz tubes with identical dimension, as described in Example 1.

As can be seen in FIG. 6, the type of quartz used for the reaction tubes has some influence on the selectivity. For example, in the HSQ tube a $C_1$ oxygenate selectivity of 28% at 9.41% $CH_4$ conversion is obtained while this value is only 24% at a conversion of 8.6% in the PS tubes.

Examining the composition of the quartz tubes, revealed some correlations with the activity and selectivity obtained for the PMO reaction in the quartz tubes. The different compositions of the impurity level and hydroxyl concentration of the quartz tubes are shown in table 1.

It seems that no obvious trends are visible between the activity/selectivity of the PMO reaction in a quartz tube and the impurity content of the quartz in terms of alkali, redox or other metals. However, the hydroxyl concentration in the quartz tubes seems to vary in a way parallel to the activity order of the different quartz tubes. PH and $GE_1$ with low activity contain concentrations of hydroxyls below 5 ppm while the more active quartz tubes (e.g. HSQ and $GE_2$) contain significantly higher OH concentrations. Generally, quartz tubes are obtained from a quartz melt solidifying around a wire of tungsten. This might lead to a small contamination of the quartz tubes with tungsten. It is known by the person skilled in the art that these surface impurities can be removed with an aqueous solution of HF. However, this was not the case for the General Electrics 1 ($GE_1$) quartz tubes and the Philips (PH) tubes. These tubes still contain the W impurities of the rod on which they were made. Only in these two types of quartz tubes no activity is observed at 0.5 MPa at temperatures below 500° C. It has never been recognised that these post-treatment with HF of quartz has an impact on chemical reactions occurring in such quartz tubes.

Example 2

Reactor Configuration and Importance of Empty Reactor Tube

Figure 7:
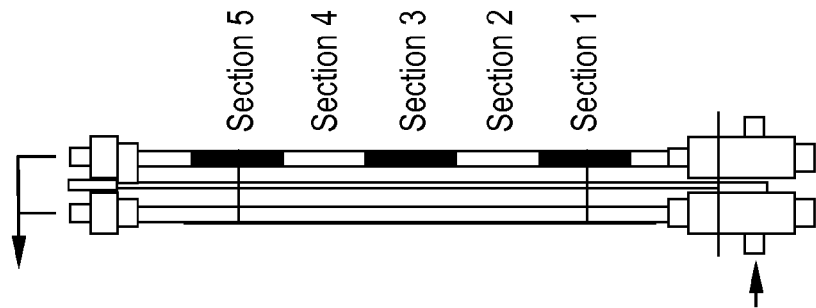
FIG. 7 is a drawing of a quartz tube reactor as described in Example 2.
Figure 8:
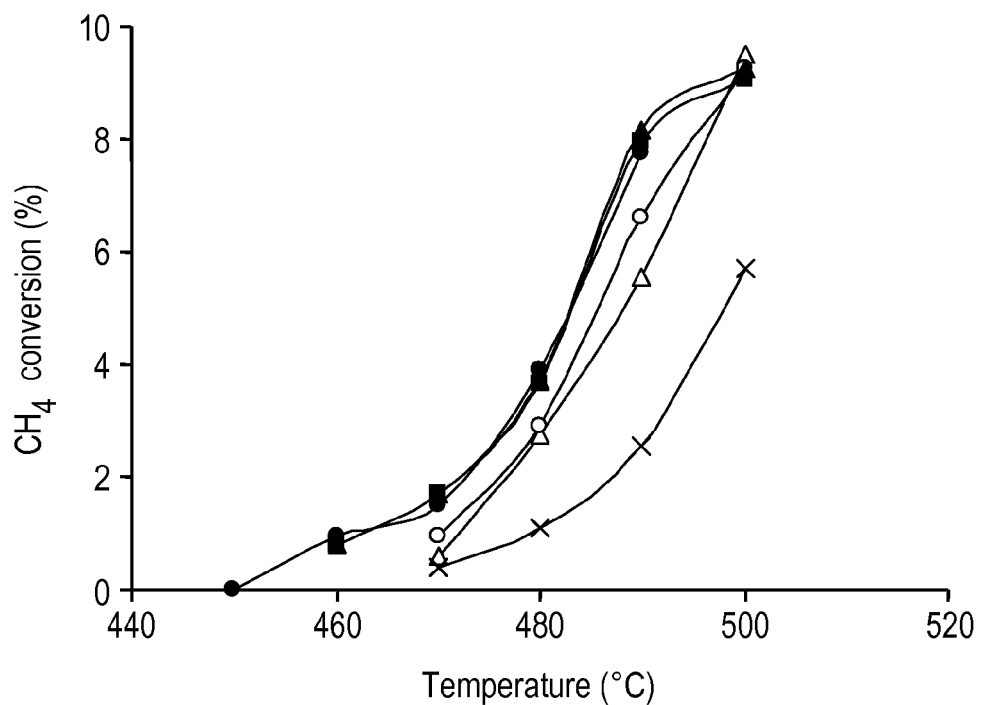
FIG. 8 is a graph of Temperature versus Methane conversion for the sections of the quartz tube reactor of FIG. 7.

In order to determine the true residence time, i.e. the time the feed reacts in the hot zone, the quartz tube was filled with quartz granules at different positions. The quartz reactor tube is always placed in a vertical furnace, divided in 5 different sections, each of 6 cm length (FIG. 7). Each time, one of the sections of the HSQ quartz tube was packed with 6 cm quartz granules (250-500 µm) and tested for the PMO reaction at 0.5 MPa (FIG. 8). Occasionally, the tube was also completely packed with quartz granules.

When the quartz granules are placed in section 2, 3 or 4, methane conversion is affected. The conversion-temperature curve is shifted to the higher temperatures when the quartz bed is placed in one of these sections. Placing quartz granules in section 1 and 5 does not affect the PMO activity. The length of the hot zone in which homogeneous gas reaction takes place is therefore 18 cm long (sum of section 2, 3 and 4), which corresponds to a reaction volume of 1.27 ml for a quartz tube with an inner diameter of 3 mm.

In standard conditions a total flow of 25 ml/min (STP) was applied and therefore the residence time in the hot zone in which reaction takes place is 5.8 s at 0.5 MPa and at 500° C.

Example 3

Effect of HF Treatment and Evaluation at 0.5 MPa

This example demonstrate that a HF treatment improves the methane conversion and improves the selectivity for oxygenates. It also increases the methanol/formaldehyde ratio from below 10 without HF treatment to higher than 15 after HF treatment.

The HSQ and Philips tubes were treated with a mixture of 20% hydrofluoric acid (HF) together with 10% phosphonic ($H_2PHO_3$) and 10% phosphoric acid ($H_3PO_4$).

Without to be bound to any theory, when HF reacts with $SiO_2$, volatile $SiF_4$ is formed (1) or in excess aqueous HF which is typically used in the quartz treatment processes, reaction 2 occurs. This HF treatment can hence remove some silicon from the surface of the quartz and generate special sites (surface defects) that influence the methane or oxygen activation.

$$4HF + SiO_2 \leftrightarrow SiF_4 + H_2O \qquad (1)$$

$$SiO_2 + 6HF \leftrightarrow H_2SiF_6 + 2H_2O \qquad (2)$$

The tubes were treated statically in a polypropylene vessel for 10 minutes. Afterwards, they were thoroughly rinsed with deionized water and dried at room temperature. They were not calcined at high temperatures, but immediately used for reaction.

Figure 9:
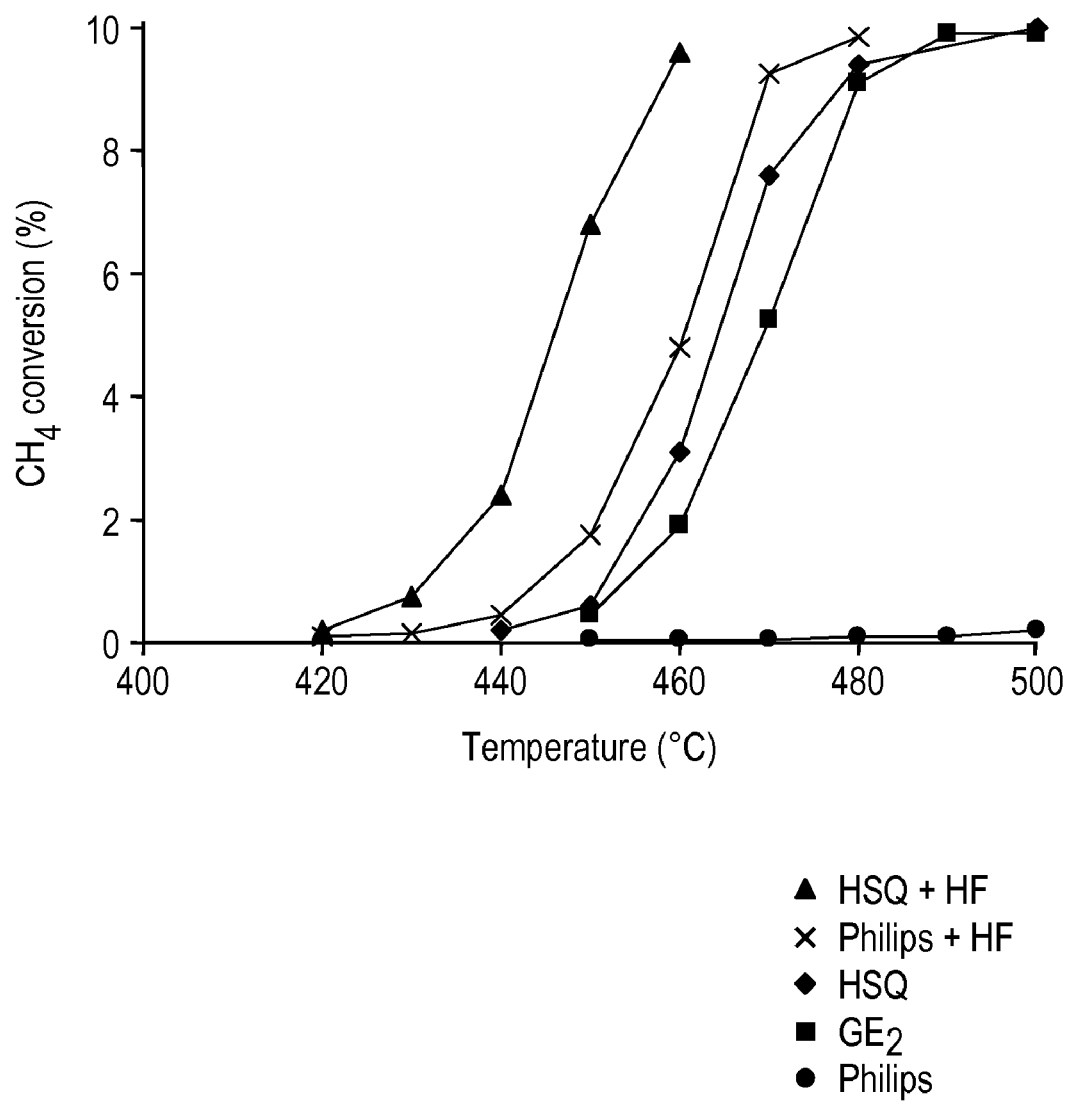
FIG. 9 is a graph of Temperature versus Methane conversion for different types of quartz tubes after treatment with HF as described in Example 3.
Figure 10:
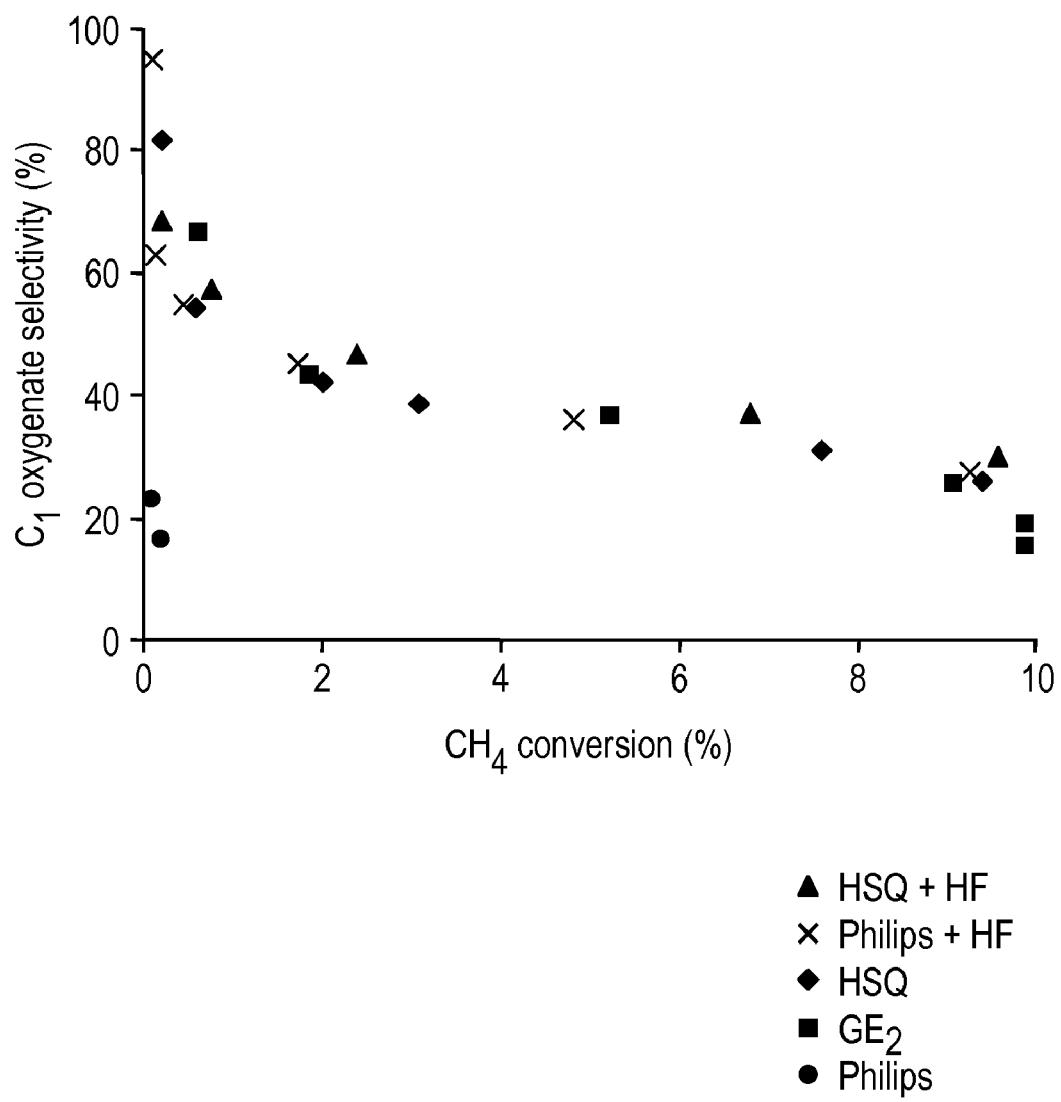
FIG. 10 is a graph of Methane conversion versus $C_1$ oxygenate selectivity for different types of quartz tubes after treatment with HF, as described in Example 3.

The methane-oxygen conversion was tested in quartz tubes of 3 mm internal diameter, corresponding to a reactor volume of 1.27 ml and a residence time of 5.8 seconds at 0.5 MPa and 500° C. The results are shown in FIGS. 9 and 10. Higher methane conversion is observed for the PMO reaction in the HF treated quartz tubes compared to the untreated quartz tubes. The effect is very significant for the Philips tubes, which are inactive at 0.5 MPa and temperatures below 500° C., when not treated with HF. The PMO reaction already starts at 440° C. in the HF treated Philips quartz tube (PH+HF) as opposed to the untreated Philips tube (PH).

The conversion-selectivity plot for different quartz tubes is show in FIG. 10. Table 2 gives a closer look to the results and more specifically to the product distribution in both the HSQ and HSQ-FHF tubes. The methanol/formaldehyde ratio increases with increasing methane conversion, e.g. in the HSQ tubes from 0.7 at 0.6% $X_{CH4}$ to 7.7 at 9.4% $X_{CH4}$ in the HSQ tubes.

TABLE 2

$C_1$ oxygenate selectivity and methanol/formaldehyde molar ratio for reaction in HSQ and HSQ + HF quartz tubes at comparable methane conversion (0.5 MPa, $CH_4/O_2$ = 9, undiluted, residence time = 5.8 s)

| HSQ | | | | HSQ + HF | | | |
|---|---|---|---|---|---|---|---|
| $X_{CH4}$ (%) | $S_{HCHO}$ (%) | $X_{CH3OH}$ (%) | CH$_3$OH/HCHO | $X_{CH4}$ (%) | $S_{HCHO}$ (%) | $S_{CH3OH}$ (%) | CH$_3$OH/HCHO |
| 0.6 | 32 | 22 | 0.7 | 0.76 | 30 | 28 | 0.9 |
| 2.0 | 13 | 29 | 2.2 | 2.4 | 8 | 38 | 4.8 |
| 9.4 | 3 | 23 | 7.7 | 9.6 | 1 | 28 | 28.0 |

The methanol/formaldehyde ratio at a certain $X_{CH4}$ conversion differs strongly for reaction in the HSQ versus the HSQ-FHF tubes. At a methane conversion of about 9.5%, i.e. 100% oxygen conversion, the methanol/formaldehyde ratio is 7.7 and 28, for the HSQ and HSQ-FHF tube, respectively. In other words, whereas the total $C_1$ oxygenate selectivity only differs slightly, the methanol selectivity is increased from 23 to 28% when the PMO reaction is performed in HSQ+HF reactor quartz tubes.

Example 4

Effect of Tube Diameter

This example demonstrates that the smaller the inner diameter, the higher the methane conversion at a given reaction temperature and the higher the selectivity for oxygenates is.

To further investigate the effect of the reactor wall on activity and selectivity and determine if this influence is beneficial or not, different quartz tubes from the same quality (PN) but with different inner diameter were tested. In order to assess this influence of the reactor wall on the gas phase oxidation, the linear velocity or residence time with the hot reaction zone needs to be identical for all tubes. Therefore the gas flow was adjusted in the 2, 3 and 4 mm tubes until the residence time was equal to 5.8 seconds.

Figure 11:
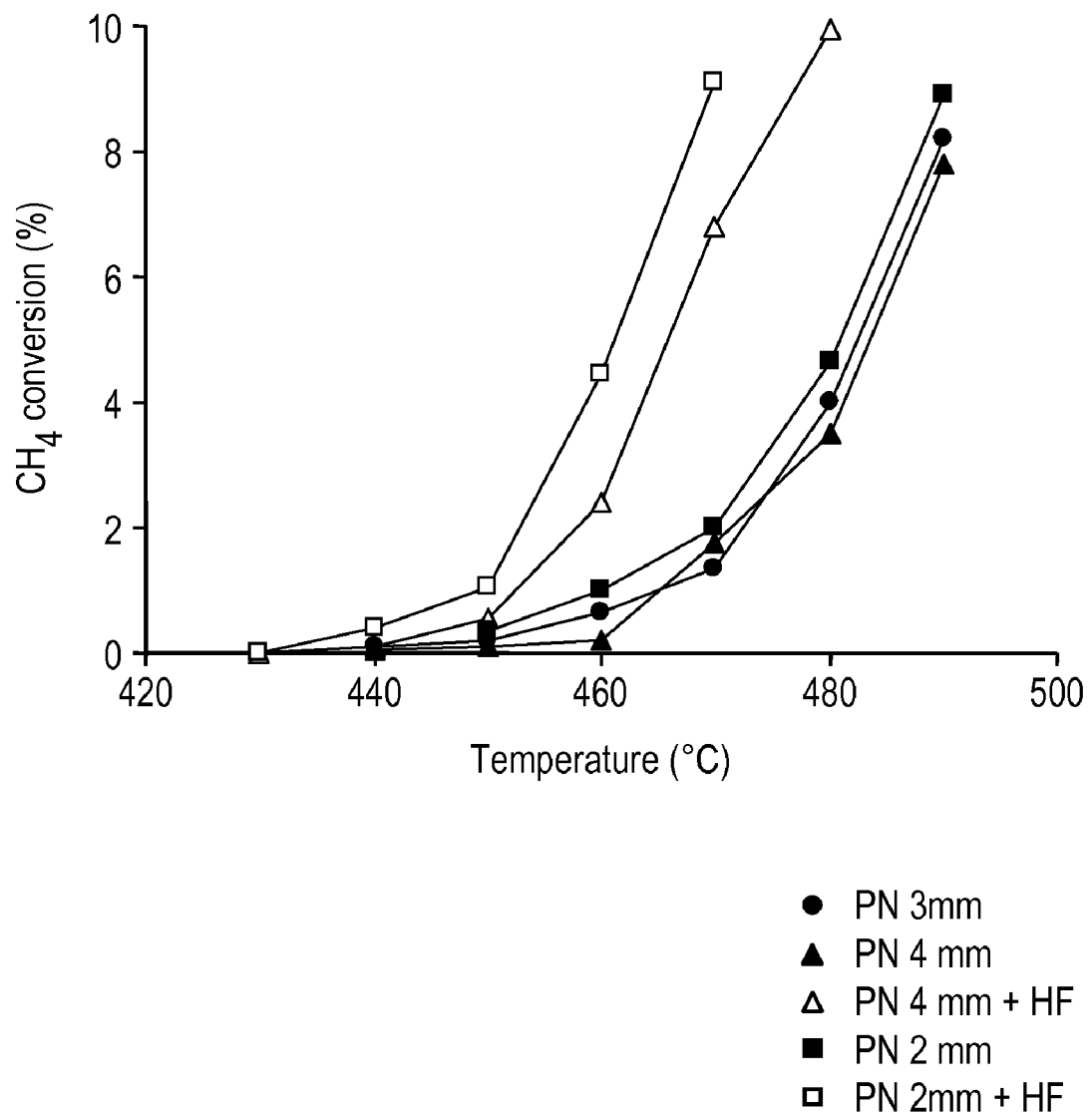
FIG. 11 is a graph of Temperature versus Methane conversion for the PMO in untreated and HF treated PN quartz tubes with different inner diameters as described in Example 4.
Figure 12:
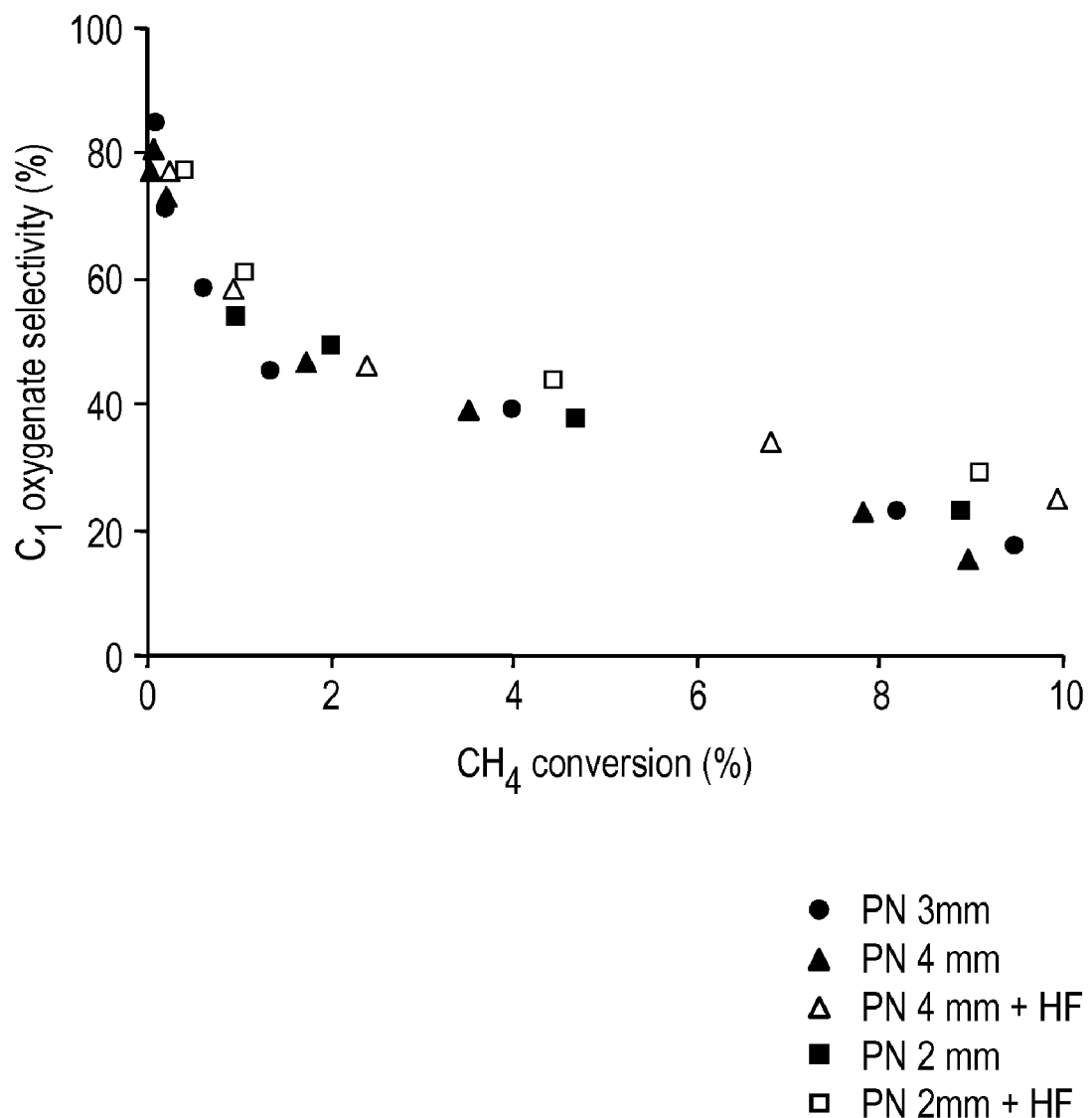
FIG. 12 is a graph of Methane conversion versus $C_1$ oxygenate selectivity for the PMO in untreated and HF treated PN quartz tubes with different inner diameters as described in Example 4.

FIGS. 11 and 12 show the results for the PMO in untreated and HF treated PN quartz tubes with different inner diameters (2, 3 and 4 mm). The methanol selectivity and yield at 100% $O_2$ conversion obtained in the three PN tubes is very similar, though lower compared the HF treated PN tubes. However, the increase in methanol yield and selectivity at 100% oxygen conversion due to the HF treatment of the quartz tube also depends on the diameter of the quartz tube (Table 3). For the 2 mm PN tube, the methanol yield increases from 2.1 to 2.8% upon HF treatment whereas it only increases from 2.1 to 2.5% in the 4 mm PN tube.

The temperature at which PMO activity starts and at which 100% $O_2$ conversion is reached, is lower with smaller tube diameter and HF treatment. The effect is lower for the tube with larger inner diameter. The activity decreases with increasing diameter which might indicate that there exists a positive (catalytic) wall effect on the activation of methane. The selectivities are very similar. The increase in activity upon HF treatment is larger for the small diameter PN quartz tubes again pointing to the existence of a beneficial (catalytic) wall effect.

MPa and 500° C. These tests have been carried out at the same residence time in the reactor of 5.8 seconds by adjusting the flow rate when the reactor is filled with particles. The quartz particles have a void fraction of 46%.

HF treated HSQ tubes were filled with granulated quartz granules (250-500 µm) over the whole length of the hot reaction zone (see example 2)

Figure 13:
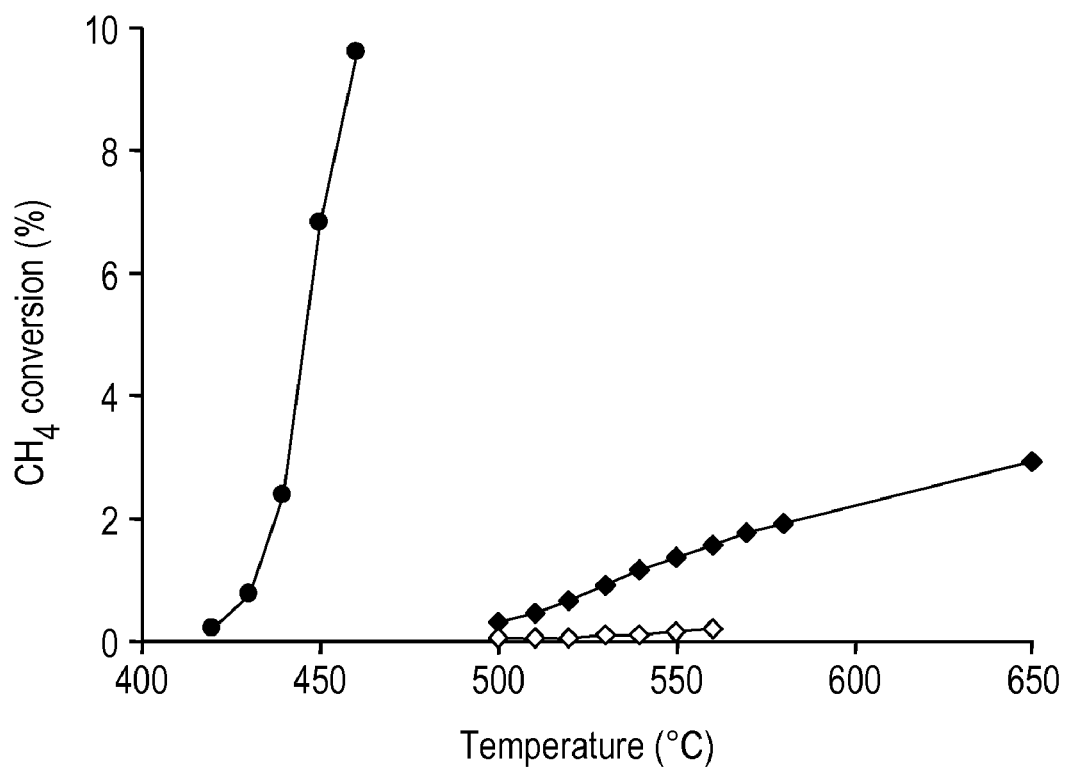
FIG. 13 is a graph of Temperature versus Methane conversion for empty treated, VWF quartz granule-filled, and VFW quartz granule-filled with HF treated quartz tubes as described in Example 5.

The results are shown in FIG. 13. The $CH_4$ conversion is much lower as compared to the empty HSQ quartz tubes. The larger surface area supplied by the packing appear to promote radical-radical terminations which accounts for the higher temperatures required.

The selectivity for both the tubes filled with HF treated and untreated quartz granules is much lower compared to the empty quartz tubes. For the empty HSQ tube and the HSQ tube filled with HF treated quartz granules, the $C_1$ selectivity at 1% $CH_4$ conversion is 53 and 29%, respectively. Furthermore, the $CO/CO_2$ ratio is much lower in the HSQ tubes filled with quartz granules compared to empty quartz tubes.

Example 6

Methanol Stability

This example demonstrates what conditions are required to maintain methanol stable under the reaction conditions. A methanol-oxygen mixture is submitted at the typical methane conversion conditions. The methanol-oxygen conversion was tested in quartz tubes of 3 mm internal diameter, corresponding to a reactor volume of 1.27 ml and a residence time of 5.8 seconds at 0.5 MPa and 500° C. The results show that below 475° C. the methanol is nearly not oxidised in presence of excess oxygen.

Methanol stability experiments were performed by feeding the reactor with a mixture of 10% $O_2$ and 5% $CH_3OH$ diluted in nitrogen. The results are shown in table 4 for empty PH tubes and HF etched HSQ tubes. Between 425 and 450° C., methanol is mainly converted to formaldehyde and some CO. Above 450° C., much more methanol is converted and mainly $CO_x$ is produced, caused by a further oxidation of HCHO.

TABLE 3

Influence of inner diameter and HF treatment of quartz tube on selectivity, yield and temperature for 100% oxygen conversion in the PMO reaction (0.5 MPa, $CH_4/O_2$ = 9, residence time = 5.8 s).

| inner diameter × outer diameter (mm) | PN | | | | PN + HF | | | |
|---|---|---|---|---|---|---|---|---|
| | $T_{100}$* (° C.) | $X_{CH4}$$ (%) | $S_{C1}$ (%) | $Y_{C1}$ (%) | $T_{100}$* (° C.) | $X_{CH4}$$ (%) | $S_{C1}$ (%) | $Y_{C1}$ (%) |
| 2 × 6 | 490 | 9.4 | 22.8 | 2.1 | 470 | 9.6 | 28.9 | 2.8 |
| 3 × 6 | 490 | 9.2 | 22.7 | 2.1 | — | — | — | — |
| 4 × 6 | 490 | 9.5 | 22.0 | 2.1 | 480 | 9.9 | 25 | 2.5 |

*$T_{100}$ = temperature (° C.) for 100% oxygen conversion
$Methane conversion at 100% oxygen conversion
$S_{C1}$ and $Y_{C1}$ are the selectivity and yield of oxygenates with one carbon Example 5 (Comparative)

Effect of Filling Reactor with Particles

This example demonstrates that the reactor tubes have to be empty. Filling the reactor with quartz particles either without or with HF treatment reduces significantly the methane conversion. The methane-oxygen conversion was tested in quartz tubes of 3 mm internal diameter, corresponding to a reactor volume of 1.27 ml and a residence time of 5.8 seconds at 0.5

However, this does not imply that during the PMO reaction some methanol converts to HCHO and/or $CO/CO_2$. At high oxygen conversion, less oxygen is available for oxidizing methanol and there will be a competition between the formation of primary products by oxidation of methane and the oxidation of methanol.

From table 4, it also follows that the reactor wall or its treatment with HF has no influence on the methanol stability.

The difference in methanol selectivity can therefore not be explained by a difference in methanol oxidation/decomposition.

TABLE 4

Methanol conversion in empty PH (above) and HSQ + HF quartz tubes (below) (0.5 MPa, $N_2/O_2/CH_3OH = 85/10/5$, Total flow = 25 ml · min$^{-1}$).

| Temperature (° C.) | 350 | 375 | 400 | 425 | 450 | 475 | 500 |
|---|---|---|---|---|---|---|---|
| $X_{CH3OH}$, % | 0.0 | 0.2 | 0.3 | 3 | 4 | 49 | 96 |
| $S_{CO}$, % | 0 | 10 | 23 | 25 | 29 | 50 | 67 |
| $S_{CO2}$, % | 0 | 0 | 2 | 3 | 2 | 27 | 33 |
| $S_{HCHO}$, % | 0 | 90 | 75 | 72 | 69 | 23 | 0 |
| Temperature (° C.) | 350 | 375 | 400 | 425 | 450 | 475 | 500 |
| $X_{CH3OH}$, % | 0.0 | 0.3 | 1 | 3 | 5 | 52 | 93 |
| $S_{CO}$, % | 0 | 12 | 23 | 26 | 22 | 48 | 70 |
| $S_{CO2}$, % | 0 | 0 | 3 | 5 | 5 | 30 | 30 |
| $S_{HCHO}$, % | 0 | 88 | 74 | 69 | 73 | 22 | 0 |

Example 7

Effect of Operating Pressure

This example demonstrates that at higher pressure the methane conversion is higher at lower temperature and also the selectivity for oxygenates is higher.

Figure 14:
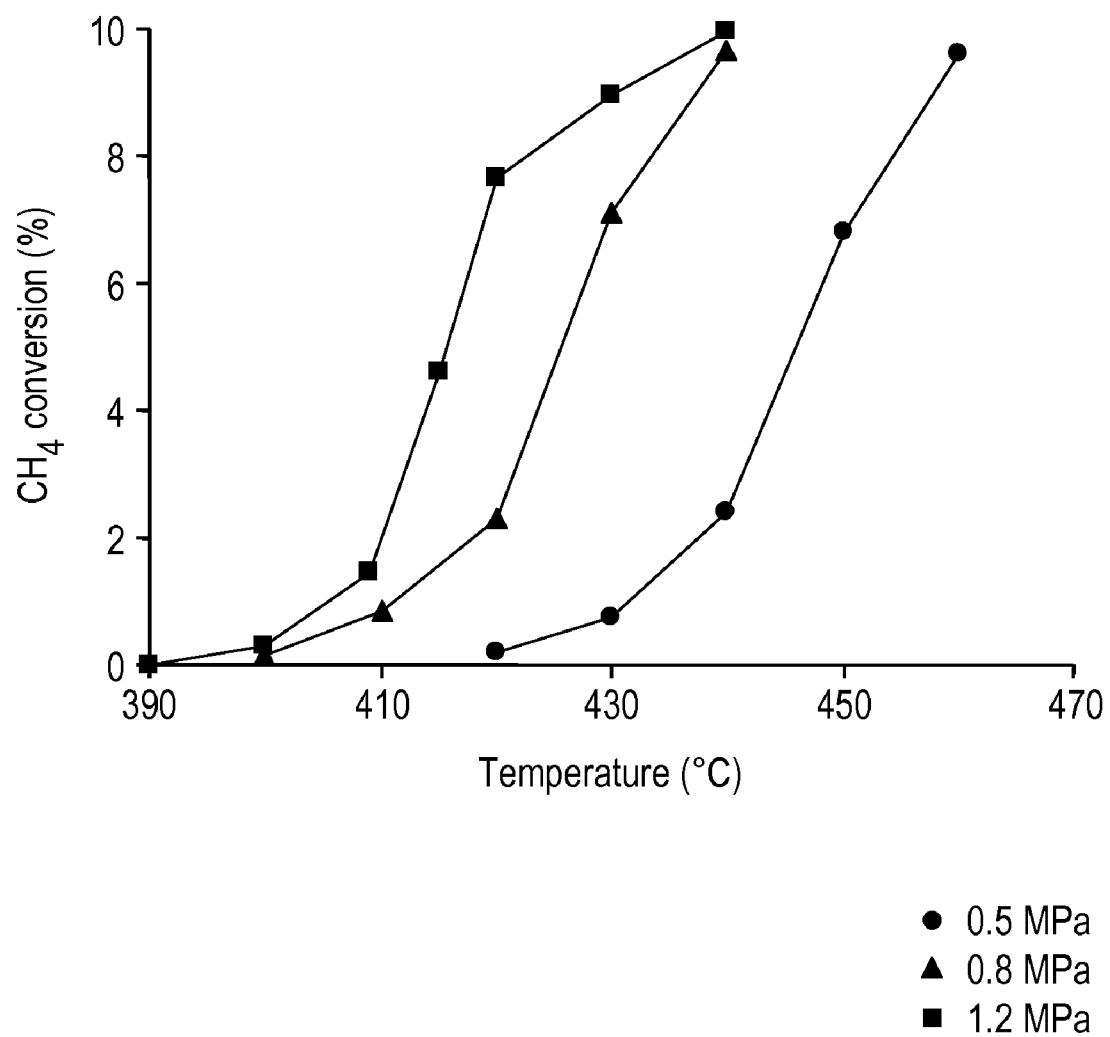
FIG. 14 is a graph of Temperature versus Methane conversion indicating the influence of pressure as described in Example 7.
Figure 15:
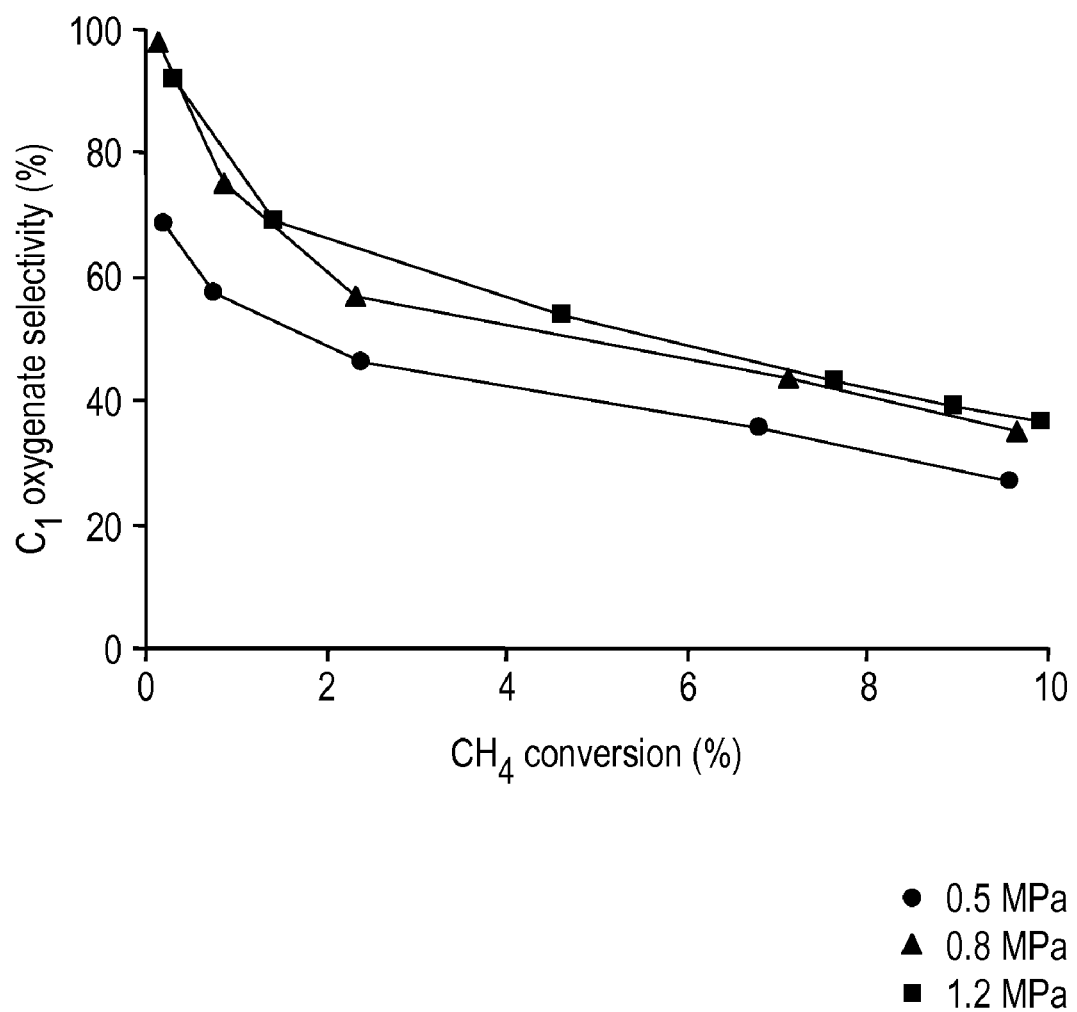
FIG. 15 is a graph of Methane conversion versus $C_1$ oxygenate selectivity indicating the influence of pressure as described in Example 7.

The methane-oxygen conversion was tested in quartz tubes of 3 mm internal diameter, corresponding to a reactor volume of 1.27 ml and a residence time at 500° C. of 5.8 seconds at 0.5 MPa, 9.3 at 0.8 MPa and 13.8 at 1.2 MPa. The influence of pressure on the activity and selectivity for the PMO in HF treated HSQ quartz tubes is shown in FIGS. 14 and 15. The methane conversion increases with increasing pressure. Already at 390° C. there is some activity detected.

Figure 16:
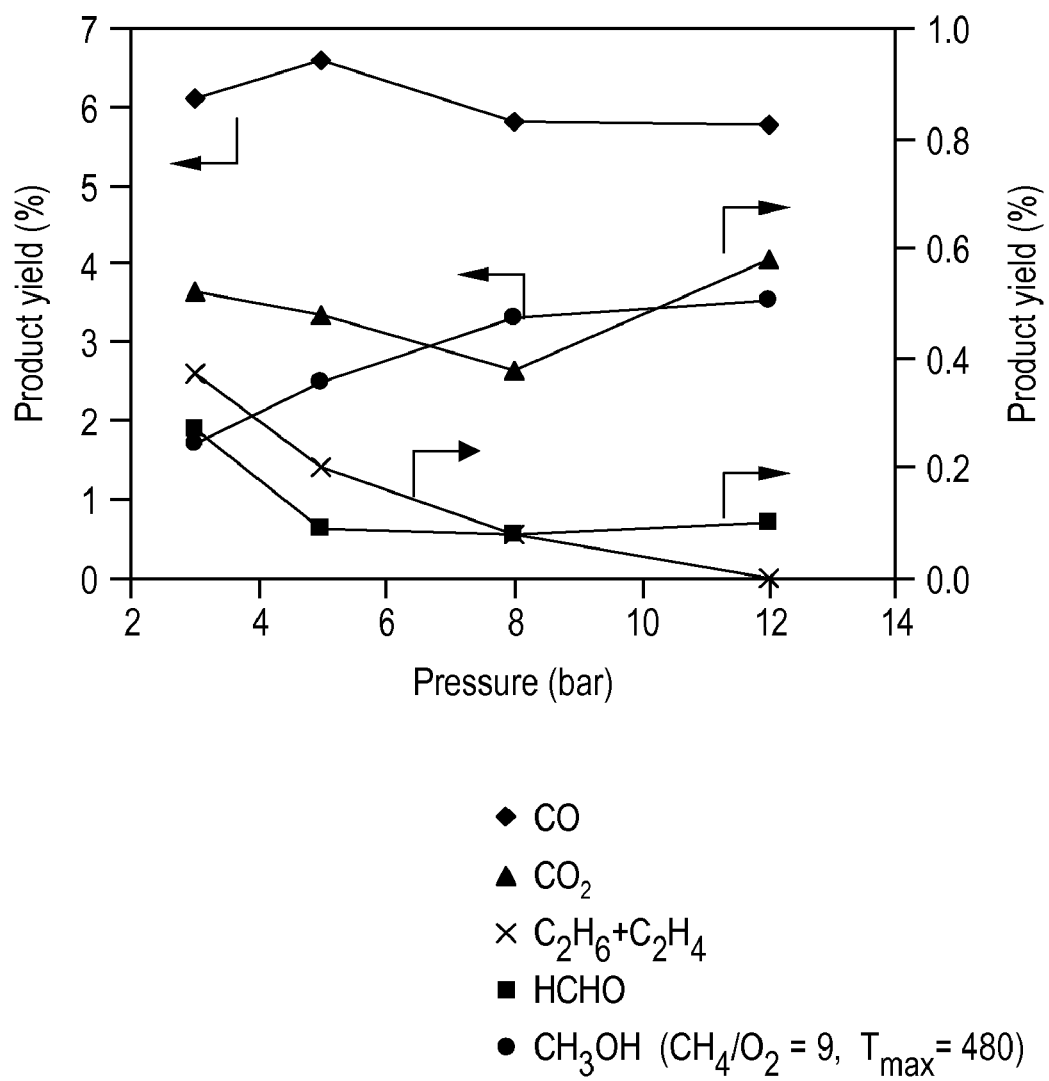
FIG. 16 is a graph of pressure versus product yield as described in Example 7.

The $C_1$ oxygenate selectivity also increases with pressure. The increase in selectivity is larger for the pressure range 0.5-0.8 MPa than for the range 0.8-1.2 MPa. The maximum $C_1$ oxygenate yield, which is almost exclusively methanol, obtained at 0.5, 0.8 and 1.2 MPa are 2.8, 3.4 and 3.6%, respectively. FIG. 16 shows the influence of operating pressure on the product yields at 100% oxygen conversion. The methanol yield increases with pressure while the HCHO yield decreases. Therefore the $CH_3OH/HCHO$ ratio increases with increasing pressure. The sum of ethylene and ethane yield decreases because the temperature, at which 100% oxygen conversion is obtained, also decreases with increasing pressure. These temperatures are 480, 460, 440 and 430° C. at 0.3, 0.5, 0.8 and 1.2 MPa, respectively.

The table 5 below gives the selectivities obtained at 1.2 MPa.

TABLE 5

Results obtained under the testing conditions of FIG. 14.

12 bar CH4/O2 = 9/1

Quartz:
HSQ + HF

| Reaction temperature ° C. | 390 | 400 | 410 | 420 | 430 | 440 |
|---|---|---|---|---|---|---|
| CH4 conversion % | 0.30 | 1.40 | 4.60 | 7.64 | 8.95 | 9.94 |
| Selectivities | | | | | | |

TABLE 5-continued

Results obtained under the testing conditions of FIG. 14.

12 bar CH4/O2 = 9/1 on C basis %

| CO | 7.7 | 24.3 | 43.3 | 50.3 | 55 | 58.6 |
|---|---|---|---|---|---|---|
| CO2 | 0.3 | 6.7 | 3.1 | 6.4 | 5.4 | 3.8 |
| C2 | 0.0 | 0.0 | 0.0 | 0.0 | 0.7 | 2.1 |
| HCHO | 57.7 | 26.0 | 14.2 | 7.7 | 4.6 | 3.5 |
| CH3OH | 34.3 | 43 | 39.4 | 35.6 | 34.3 | 32 |

These data show that little CO2 is produced. CO has still a value and can be used for the production of hydrogen through the watergas shift reaction:

$$CO + H2O \leftrightarrow CO2 + H2$$

Example 8

Effect of Reactor Tube Diameter

Table 6 shows the results for PMO reaction at 0.8 MPa in the HF treated PN tubes with different internal diameters (2 and 4 mm) but equal residence time of 9.3 seconds in the hot zone. As was the case at 0.5 MPa, the smaller diameter HF treated PN tube show a higher activity and selectivity compared to the HF treated 4 mm PN tube. The maximum methanol yield is 2.8% with 29% selectivity for the 4 mm tube while it is 3.3% with 33% selectivity for the 2 mm tube.

TABLE 6

Influence of inner diameter and HF treatment of quartz tube on the selectivity, yield and temperature of 100% oxygen conversion in the PMO reaction at 0.8 MPa ($CH_4/O_2 = 9$, undiluted, residence time = 9.3 s)

| Inner diameter × outer diameter (mm) | PN + HF | | | |
|---|---|---|---|---|
| | $T_{100}$* (° C.) | $X_{CH4}$$ (%) | $S_{C1}$ (%) | $Y_{C1}$ (%) |
| 2 × 6 | 450 | 9.7 | 34 | 3.3 |
| 4 × 6 | 460 | 9.6 | 29 | 2.8 |

*$T_{100}$ = temperature (° C.) for 100% oxygen conversion
$Methane conversion at 100% oxygen conversion
$S_{C1}$ and $Y_{C1}$ are the selectivity and yield of oxygenates with one carbon

The invention claimed is:

1. A process for converting methane to methanol, comprising: feeding methane and an oxygen-containing gas selected from the group consisting of gaseous air, oxygen, and gaseous air enriched with oxygen to a reactor under an elevated pressure; wherein the reactor comprises an internal surface, wherein the internal surface is made of quartz or coated with quartz having a concentration of hydroxyls of at least 5 ppm, surrounding a reaction zone in which the methane and oxygen-containing gas react; reacting the methane and oxygen-containing gas in the reaction zone at an elevated temperature effective to produce products selected from the group consisting of methanol and valuable oxygenates and combinations thereof.

2. The process of claim 1, wherein the internal surface, made of silica or coated with silica, is treated with a mixture of HF and phosphonic acid before the conversion of methane to methanol.

3. The process of claim 1, wherein the reaction is carried out in the absence of any added material that measurably affects the rate of the reaction or the yield of the product.

4. The process of claim 1, wherein the reactor is operated under a pressure of from 0.1 to 7.5 MPa.

5. The process of claim 4, wherein the reactor is operated under a pressure of from 0.2 to 5 MPa.

6. The process of claim 1, wherein the methane and oxygen-containing gas are fed to the reactor in amounts resulting in a methane to oxygen molar ratio of from 1 to 50.

7. The process of claim 6, wherein the methane and oxygen-containing gas are fed to the reactor in amounts resulting in a methane to oxygen molar ratio of from 2 to 20.

8. The process of claim 1, further comprising a residence time in the reactor at a required reaction temperature and pressure of from 0.1 to 100 seconds.

9. The process of claim 8, wherein the residence time in the reactor at the required reaction temperature and pressure is from 1 to 75 seconds.

10. The process of claim 8, wherein the residence time in the reactor at the required reaction temperature and pressure is from 2 to 20 seconds.

11. The process of claim 1, wherein the reactor is operated at a temperature of from 300° C. to 600° C.

12. The process of claim 11, wherein the temperature is from 400° C. to 450° C.

13. A reactor for converting methane to methanol, comprising a reactor vessel having an internal surface made of quartz or coated with quartz having a concentration of hydroxyls of at least 5 ppm.

14. The reactor of claim 13, further comprising multiple tubes of a given inner diameter placed in parallel in the reactor vessel so as to obtain a multi-tubular reactor comprising a specific surface-to-volume ratio.

15. The reactor of claim 14, wherein the inner diameter of the multiple tubes is from 2 to 10 mm.

16. The reactor of claim 14, wherein reactants enter on one side of the multiple tubes and reaction products leave on the opposite side of the multiple tubes.

17. The reactor of claim 14, wherein the multiple tubes are placed parallel and linked at the top or bottom of the reactor vessel to a manifold device in such a manner that the reactants can only flow in one direction inside the multiple tubes and in the other direction outside of the multiple tubes.

18. The reactor of claim 13, wherein the reactor comprises multiple plates, wherein the plates are arranged within the reactor creating a distance between the plates such that an optimum surface-to-volume ratio and residence time is obtained.

19. The reactor of claim 18, wherein the arrangement of the plates creates a heat exchange between a cold entering gas and a hot leaving gas.

* * * * *